(12) United States Patent
Graus Ferrer et al.

(10) Patent No.: US 11,439,722 B2
(45) Date of Patent: Sep. 13, 2022

(54) DEVICE FOR EVAPORATING VOLATILE SUBSTANCES

(71) Applicant: ZOBELE HOLDING SPA, Trento (IT)

(72) Inventors: Alba Graus Ferrer, Barcelona (ES); Asa Jonsson, Barcelona (ES); Jordi Maso Sabate, Barcelona (ES)

(73) Assignee: ZOBELE HOLDING S.P.A.

( * ) Notice: Subject to any disclaimer, the term of this patent is extended or adjusted under 35 U.S.C. 154(b) by 965 days.

(21) Appl. No.: 16/303,782

(22) PCT Filed: May 22, 2017

(86) PCT No.: PCT/EP2017/062245
§ 371 (c)(1),
(2) Date: Nov. 21, 2018

(87) PCT Pub. No.: WO2017/202760
PCT Pub. Date: Nov. 30, 2017

(65) Prior Publication Data
US 2020/0316242 A1    Oct. 8, 2020

(30) Foreign Application Priority Data

May 23, 2016  (ES) ............................... ES201630661

(51) Int. Cl.
*A61L 9/012* (2006.01)
*A61L 9/12* (2006.01)

(52) U.S. Cl.
CPC ................. *A61L 9/12* (2013.01); *A61L 9/012* (2013.01); *A61L 2209/131* (2013.01); *A61L 2209/133* (2013.01)

(58) Field of Classification Search
CPC ...... A61L 9/12; A61L 9/012; A61L 2209/131; A61L 2209/133
See application file for complete search history.

(56) References Cited

FOREIGN PATENT DOCUMENTS

| | | |
|---|---|---|
| DE | 297 00 718 U1 | 4/1997 |
| EP | 2 712 632 A1 | 4/2014 |
| JP | H08-196610 A | 8/1996 |
| WO | WO 2007/064538 A1 | 6/2007 |
| WO | WO 2007/071082 A1 | 6/2007 |
| WO | WO 2011/042232 A1 | 4/2011 |

OTHER PUBLICATIONS

International Search Report dated Sep. 19, 2017 in corresponding PCT International Application No. PCT/EP2017/062245.
Written Opinion dated Sep. 19, 2017 in corresponding PCT International Application No. PCT/EP2017/062245.

*Primary Examiner* — Alma Pipic
(74) *Attorney, Agent, or Firm* — Ostrolenk Faber LLP

(57) ABSTRACT

A device for evaporating volatile substances including a solid body impregnated with volatile substances and a support for the solid body. The solid body includes a protrusion defining on the inside thereof a housing and the solid body includes a hole, inside of which the protrusion is placed, such that the device further includes a container to house a liquid which impregnates the solid body with volatile substances. The device allows the solid body to be correctly held in the support during the entire useful life thereof. Furthermore, due to the presence of the container with liquid, the user may know if the device is still evaporating the volatile substances correctly or if it must be replaced.

10 Claims, 1 Drawing Sheet

DEVICE FOR EVAPORATING VOLATILE SUBSTANCES

CROSS-REFERENCE TO RELATED APPLICATIONS

The present application is a 35 U.S.C. §§ 371 national phase conversion of PCT/EP2017/062245, filed May 22, 2017, which claims priority to Spanish Patent Application No. P201630661, filed May 23, 2016, the entire contents of both applications being incorporated herein by reference. The PCT International Application was published in the English language.

The present invention relates to a device for evaporating volatile substances, said volatile substances impregnated in a solid body, which has the function of indicating the end of the useful life of the device and of maintaining the evaporation body in position.

BACKGROUND OF THE INVENTION

Among known air fresheners, there is currently a category of air fresheners in which the volatile substances evaporate from a solid impregnated body, generally made up of a plastic material impregnated with fragrances or perfumed gels.

These types of air fresheners have the advantage in that they have a very simple design, generally consisting of a body made of plastic or gel and a support to avoid the direct contact between the perfumed body and the area on which the air freshener is placed, for example, the dashboard of a car, and also to allow for the correct positioning thereof, for example, hanging on a cabinet, etc.

One drawback of these types of devices is that the impregnated solid body changes size during the lifespan of the product, since as the fragrance evaporates and the size of the body decreases.

This is a problem when the impregnated plastic and the support are joined together simply by mechanical interference. The level of interference that guarantees the connection when the device is new changes during the continual contraction of the impregnated plastic and may cause the impregnated plastic of the support to fall.

Another drawback of these types of devices is that they do not have an indicator to show the useful life of the device, meaning that the user does not know when the device must be replaced because of an insufficient level of evaporation.

Therefore, it is clear that there is a need for a device for evaporating volatile substances wherein the solid impregnated body is held during the entire useful life of the device and has an indicator to show the useful life thereof so that the user knows when it must be changed.

DESCRIPTION OF THE INVENTION

The device of the invention resolves the aforementioned drawbacks and has other advantages which are described below.

The device for evaporating volatile substances according to the present invention comprises a solid body impregnated with said volatile substances and a support for said solid body, and is characterized in that said solid body comprises a protrusion defining on the inside thereof a housing, and said solid body comprising a complementary hole, inside of which said protrusion is placed, such that the device further comprises a container to house a volatile liquid.

Advantageously, the container is placed inside said housing through the hole of the solid body.

According to a preferred embodiment, said container comprises a flange which is placed on a lowered portion of the solid body around the hole thereof.

Moreover, said container preferably comprises a semipermeable membrane which covers said liquid, said semipermeable membrane being covered by a protective film before the device is used for the first time.

Preferably, said protrusion of the support has a tubular shape and said solid body is disc-shaped, which may be made of a polyethylene vinyl acetate copolymer impregnated with perfume. Alternatively, the solid body could be made up of a solid gel, of the known types, for example, of the carrageenan type.

Furthermore, the support may have a concave shape to contain the solid body.

The device for evaporating volatile substances according to the present invention has the advantage in that the solid body is correctly held in the support during the entire useful life thereof. Furthermore, thanks to the presence of the container with liquid, the user may know if the device is still evaporating the volatile substances correctly or if it must be replaced.

BRIEF DESCRIPTION OF THE DRAWINGS

For the purpose of helping to make the foregoing description more readily understandable, it is accompanied by a set of drawings which, schematically and by way of illustration and not limitation, represent an embodiment.

DESCRIPTION OF A PREFERRED EMBODIMENT

Figure 1:
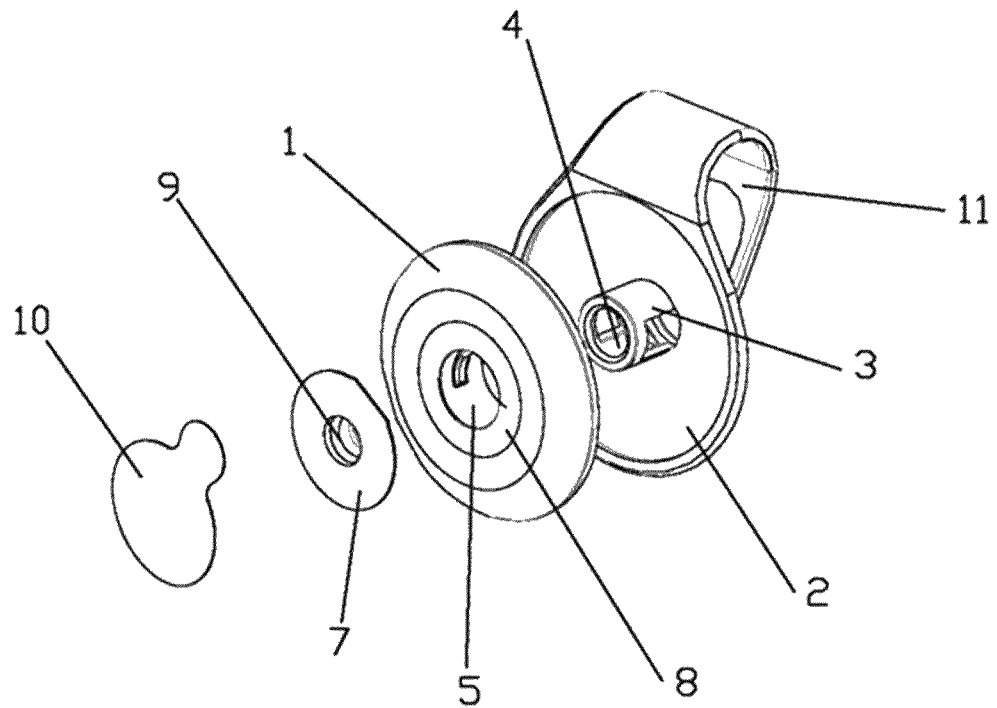
FIG. 1 is an exploded perspective view of the device for evaporating volatile substances according to the present invention.
Figure 2:
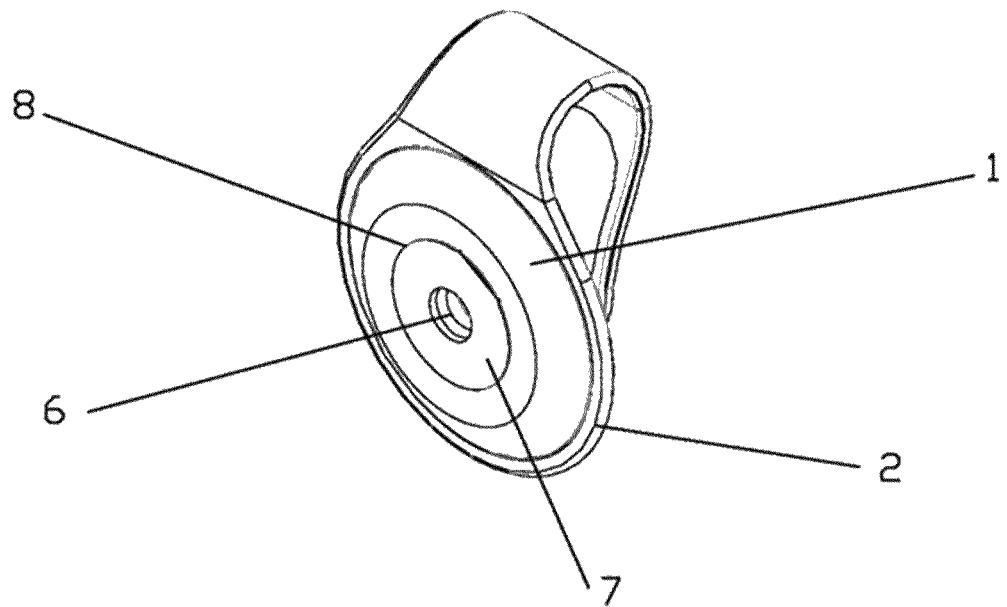
FIG. 2 is a perspective view of the device for evaporating volatile substances according to the present invention in its assembled position.

The device for evaporating volatile substances according to the present invention comprises a solid body 1 which is impregnated with volatile substances, such as perfume. Said solid body 1 is preferably disc-shaped, although it could be any shape that is suitable to the invention.

Said solid body 1 is mounted on a support 2, for example in a concave shape, and said support 2 comprises a protrusion 3, for example in a tubular shape, said protrusion 3 housed in a complementary hole 5 of the solid body 1. The support may comprise a clip 11 or any suitable means for the fastening thereof to an external element.

Said protrusion 3 also defines a housing 4, the inside of which houses a container 6 which contains a liquid through said hole 5 of the solid body 1, as can be seen in the figures.

Said container 6 is cup-shaped and comprises a flange 7, which is placed above the solid body. Alternatively, a lowered portion 8 of said solid body 1 may be designed, as seen in the figures, for aesthetic reasons, such that the flange does not protrude from the upper plane of the solid body. Thanks to this flange, it is guaranteed that the solid body cannot come out of its position throughout the useful life of the product due to the variations of the solid body when the perfume evaporates.

To do so, the flange of the container must be of a dimension greater than the thickness of the protrusion where it is located. Preferably, this dimension is between 2 and 5 mm.

Moreover, it is possible that, without modifying the general aesthetics of the device, one may want to limit the olfactory intensity of the device, and in doing so, limit the evaporation rate. To this end, a greater dimension of the flange may be considered, in order to cover a greater surface dimension of the solid body, thereby limiting the effective evaporation surface of said porous body. To do so, the dimension of the flange could be greater than 10 mm.

Moreover, said container 6 comprises a semi-permeable membrane 9, which allows for the impregnation of the solid body 1 with the liquid of the container, also allowing the evaporation thereof through the same. To avoid evaporation before the first use, said semi-permeable membrane 9 is protected by a protective film 10, which is removed by the user before using the device for the first time.

In a preferred embodiment, the solid body 1 is made up of a polyethylene vinyl acetate copolymer, impregnated with perfume, for example, in a weight proportion of 25%.

Moreover, the support 2 may be made from polypropylene, and the container may be made from thermoplastic, such as PET/PE.

Said semi-permeable membrane 9 preferably comprises multiple layers and may be made from polyethylene with a thickness of 40 microns, for example, laminated with said protective film, for example with aluminum.

The liquid in the container 6 may be composed of and aliphatic solvent with a dye, and may contain a fragrance.

Said container 6 may be held inside the protrusion 3 by mechanic interference, or may be soldered to the protrusion 3 by means of heat or ultrasonic soldering.

To use the device, the user simply has to remove the protective film 10, allowing the solid body 1 to be impregnated with the liquid inside the container 6 and the volatile substances to be evaporated.

When the liquid inside the container 6 has been depleted, which may be seen from outside the device, the user therefore knows that the device must be changed, since it will no longer function in a proper way.

Despite the fact that reference has been made to a specific embodiment of the invention, it is evident for a person skilled in the art that numerous variations and changes may be made to the device described, and that all the aforementioned details may be substituted by other technically equivalent ones, without detracting from the scope of protection defined by the attached claims.

The invention claimed is:

1. A device for evaporating volatile substances comprising:
   a solid body configured to be impregnated with said volatile substances;
   a support for said solid body, said support including a protrusion defining on the inside thereof a housing;
   said solid body comprising a hole, inside of which said protrusion is placed; and
   a container configured to house a liquid which impregnates said solid body with said volatile substances.

2. The device for evaporating volatile substances according to claim 1, wherein the container is placed inside said housing through the hole of the solid body.

3. The device for evaporating volatile substances according to claim 1, wherein said container comprises a flange which is placed on an outer surface of the solid body.

4. The device for evaporating volatile substances according to claim 3, wherein said flange is placed on the solid body around the hole thereof.

5. The device for evaporating volatile substances according to claim 1, wherein said container contains said liquid and said container comprises a semi-permeable membrane which covers said liquid.

6. The device for evaporating volatile substances according to claim 5, wherein said semi-permeable membrane is covered by a removable protective film.

7. The device for evaporating volatile substances according to claim 1, wherein said protrusion of the support has a tubular shape.

8. The device for evaporating volatile substances according to claim 1, wherein said solid body is disc-shaped.

9. The device for evaporating volatile substances according to claim 1, wherein said solid body comprises a polyethylene vinyl acetate copolymer impregnated with perfume.

10. The device for evaporating volatile substances according to claim 1, wherein the support has a concave shape to contain the solid body.

* * * * *